(12) United States Patent
Bose et al.

(10) Patent No.: US 11,908,134 B2
(45) Date of Patent: *Feb. 20, 2024

(54) SYSTEMS AND METHODS FOR ERROR CHECKING IN RADIOTHERAPY TREATMENT REPLANNING

(71) Applicant: SHANGHAI UNITED IMAGING HEALTHCARE CO., LTD., Shanghai (CN)

(72) Inventors: Supratik Bose, Houston, TX (US); Jonathan Maltz, Houston, TX (US); Johannes Stahl, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/805,683

(22) Filed: Jun. 6, 2022

(65) Prior Publication Data
US 2022/0309662 A1 Sep. 29, 2022

Related U.S. Application Data

(63) Continuation of application No. 16/728,078, filed on Dec. 27, 2019, now Pat. No. 11,354,800.

(51) Int. Cl.
G06T 7/00 (2017.01)
G06T 7/11 (2017.01)
(Continued)

(52) U.S. Cl.
CPC ............ *G06T 7/0012* (2013.01); *A61N 5/103* (2013.01); *G06T 7/11* (2017.01); *G06T 7/149* (2017.01);
(Continued)

(58) Field of Classification Search
CPC ......... G06T 7/0012; G06T 7/11; G06T 7/149; G06T 7/337; G06T 7/62;
(Continued)

(56) References Cited

U.S. PATENT DOCUMENTS 11,354,800 B2 * 6/2022 Bose .................... A61N 5/1038
11,395,926 B2 * 7/2022 Isola ...................... G16H 20/40
(Continued)

FOREIGN PATENT DOCUMENTS

CA 2905989 A1 1/2008
CN 104117151 A 10/2014
(Continued)

OTHER PUBLICATIONS

Cao, Ximiao et al., A Survey on Evaluation Methods for Medical Image Registration, 2007 IEEE/ICME International Conference on Complex Medical Engineering, 718-721, 2007.
(Continued)

*Primary Examiner* — Jon Chang
(74) *Attorney, Agent, or Firm* — METIS IP LLC

(57) ABSTRACT

A method for adaptive treatment planning is provided. The method may include obtaining a planning image volume of a subject, a treatment image volume of the subject, and a first treatment plan related to the planning image volume of the subject, each of the planning image volume and the treatment image volume including an ROI of the subject. The method may also include registering the planning image volume and the treatment image volume, and determining a first contour of the ROI in the registered planning image volume and a second contour of the ROI in the registered treatment image volume. The method may also include evaluating whether an error exists in at least one of the registration or the contour determination based on the first contour and the second contour, and determining a second
(Continued)

treatment plan with respect to the treatment image volume based on the evaluation result.

20 Claims, 6 Drawing Sheets

(51) Int. Cl.
  *G06T 7/149* (2017.01)
  *G06T 7/33* (2017.01)
  *A61N 5/10* (2006.01)
  *G06T 7/62* (2017.01)

(52) U.S. Cl.
  CPC .............. *G06T 7/337* (2017.01); *G06T 7/62* (2017.01); *A61N 5/1071* (2013.01); *G06T 2207/20116* (2013.01); *G06T 2207/30004* (2013.01)

(58) Field of Classification Search
  CPC . G06T 2207/20116; G06T 2207/30004; G06T 2207/10081; G06T 2207/10088; G06T 2207/10104; G06T 2207/10108; G06T 2207/10116; G06T 2207/20076; G06T 2207/20224; G06T 2207/30024; G06T 2207/30096; G06T 7/0014; G06T 7/0016; G06T 7/33; A61N 5/103; A61N 5/1071; A61N 5/1038
  See application file for complete search history.

(56) References Cited

U.S. PATENT DOCUMENTS

| | | |
|---|---|---|
| 2007/0043286 A1 | 2/2007 | Lu et al. |
| 2009/0005668 A1 | 1/2009 | West et al. |
| 2015/0297916 A1* | 10/2015 | Chen .................. G06T 7/13 600/1 |
| 2019/0099619 A1 | 4/2019 | Maltz |
| 2021/0069527 A1 | 3/2021 | Peltola et al. |
| 2021/0177357 A1 | 6/2021 | Yang et al. |

FOREIGN PATENT DOCUMENTS

| | | |
|---|---|---|
| CN | 104548372 A | 4/2015 |
| RU | 2017124352 A3 | 1/2019 |

OTHER PUBLICATIONS

Rojano Kashani et al., Objective Assessment of Deformable Image Registration in Radiotherapy: A Multi-institution Study, Med. Phys., 35(12): 5944-5953, 2008.

Raj Varadhan et al., A Framework for Deformable Image Registration Validation in Radiotherapy Clinical Applications, Journal of Applied Clinical Medical Physics, 14(1): 192-213, 2013.

Li, Xin et al., Comprehensive Evaluation of Ten Deformable Image Registration Algorithms for Contour Propagation between CT and Cone-beam CT Images in Adaptive Head & Neck Radiotherapy, PLOS One, 2017, 17 pages.

Noriyuki Kadoya et al., Evaluation of Various Deformable Image Registration Algorithms for Thoracic Images, Journal of Radiation Research, 55: 175-182, 2014.

Neil Kirby et al., An Automated Deformable Image Registration Evaluation of Confidence Tool, Physics in Medicine & Biology, 61: 203-214, 2016.

Patrik F. Raudaschl et al., Evaluation of Segmentation Methods on Head and Neck CT: Auto-segmentation Challenge 2015, Med. Phys., 44(5): 2020-2036, 2017.

Courtenay L. Glisson et al., Comparison and Assessment of Semi-automatic Image Segmentation in Computed Tomography Scans for Image-guided Kidney Surgery, Med. Phys., 38(11): 6265-6274, 2011.

Tomasz Weglinski et al., Survey of Modern Image Segmentation Algorithms On CT Scans of Hydrocephalic Brains, Image Processing & Communication, 17(4): 223-230, 2015.

"Dose-Volume Histogram", Web page <https://www.slideshare.net/sasikumars/dose-volume-histogram>, Apr. 18, 2014.

D. Ruan et al., Evolving Treatment Plan Quality Criteria from Institution-specific Experience, Med. Phys., 39(5): 2708-2712, 2012.

J. C. L. Aifonso et al., A Dose-volume Histogram Based Decision-support System for Dosimetric Comparison of Radiotherapy Treatment Plans, Radiation Oncology, 2015, 9 pages.

K. M. Langen et al., Organ Motion and Its Management, Int. J. Radiation Oncology Biol. Phys., 50(1): 265- 278, 2001.

"The MatchPoint Registration Evaluation View", Web page <https://docs.mitk.org/2017.07/org_mitk_gui_qt_matchpoint_evaluator.html>, Jul. 2017.

"Radiotherapy Plan Evaluation in Brain Tumours", Web page <https://www.slideshare.net/ashutoshmukherji/radiotherapy-plan-evaluation-in-brain-tumours>, Feb. 15, 2014.

First Office Action in Chinese Application No. 202011561821.4 dated Jun. 6, 2022, 10 pages.

* cited by examiner

SYSTEMS AND METHODS FOR ERROR CHECKING IN RADIOTHERAPY TREATMENT REPLANNING

CROSS-REFERENCE TO RELATED APPLICATIONS

This application is a continuation of U.S. patent application Ser. No. 16/728,078, filed on Dec. 27, 2019, the contents of which are hereby incorporated by reference.

TECHNICAL FIELD

The present disclosure generally relates to systems and methods for radiotherapy (RT), and more particularly, to systems and methods for error checking in radiotherapy treatment replanning.

BACKGROUND

Radiotherapy is widely used in clinical treatment for cancers and other conditions. Conventionally, a treatment plan for a cancer patient is generated before treatment starts. The treatment plan may be delivered to the patient during several treatment fractions, spread over a treatment period of multiple days (e.g., 2 to 5 weeks). However, during the treatment period, an anatomical change (e.g., weight loss, growth, shrinkage, or disappearance of a tumor, the appearance of a new tumor, etc.) may take place within the patient. The size and/or position of a certain organ may change between the time of planning and the time of a treatment fraction. Accordingly, the treatment plan may need to be verified and/or updated before the treatment fraction. For example, a scan, such as a computed tomography (CT) scan or a magnetic resonance imaging (MRI) scan may be performed before the treatment fraction to acquire a treatment image of the subject. If the treatment image indicates that an anatomical change is significant, replanning may be performed to generate a modified plan. Thus, it may be desirable to develop effective systems and methods for error checking in RT treatment replanning, thereby improving the replanning accuracy.

SUMMARY

According to an aspect of the present disclosure, a system may include at least one storage device including a set of instructions for adaptive treatment planning, and at least one processor configured to communicate with the at least one storage device. When executing the set of instructions, the at least one processor may be configured to direct the system to perform operations including obtaining a planning image volume of a subject, a treatment image volume of the subject, and a first treatment plan related to the planning image volume of the subject, each of the planning image volume and the treatment image volume including a region of interest (ROI) of the subject. The operations may further include registering the planning image volume and the treatment image volume with respect to a common coordinate system, and determining a first contour of the ROI in the registered planning image volume and a second contour of the ROI in the registered treatment image volume. The operations may also include obtaining an evaluation result by evaluating whether an error exists in at least one of the registration or the contour determination based on the first contour and the second contour, and determining a second treatment plan with respect to the treatment image volume based on the evaluation result.

In some embodiments, the evaluation result may include that an error exists in neither the registration nor the contour determination. To determine a second treatment plan with respect to the treatment image volume, the at least one processor may be further configured to direct the system to perform additional operations including obtaining a determination result by determining whether the first treatment plan needs to be modified, and determining the second treatment plan based on the evaluation result and the determination result.

In some embodiments, the determination result may include that the first treatment plan needs to be modified. To determine the second treatment plan based on the evaluation result and the determination result, the at least one processor may be further configured to direct the system to perform additional operations including generating a modified treatment plan by modifying the first treatment plan, and designating the modified treatment plan as the second treatment plan.

In some embodiments, the at least one processor may be further configured to direct the system to perform additional operations including obtaining a second evaluation result by evaluating whether a second error exists in the generation of the modified treatment plan, and in response to the second evaluation result that the second error exists in the generation of the modified treatment plan. The generation of the modifying treatment plan may including generating the modified treatment plan by further modifying the modified treatment plan or modifying the first treatment plan.

In some embodiments, to evaluate whether a second error exists in the generation of the modified treatment plan, the at least one processor may be further configured to direct the system to perform additional operations including determining one or more characteristic spots in the registered treatment image volume based on the modified treatment plan, and evaluating whether a second error exists in the generation of the modified treatment plan based on the one or more characteristic spots in the registered treatment image volume.

In some embodiments, to determine one or more characteristic spots in the registered treatment image volume, the at least one processor may be further configured to direct the system to perform additional operations including determining one or more characteristic spots in the registered planning image volume, and determining the one or more characteristic spots in the registered treatment image volume based on the one or more characteristic spots in the registered planning image volume.

In some embodiments, the determination result may include that the first treatment plan does not need to be modified, and the determining the second treatment plan includes designating the first treatment plan as the second treatment plan.

In some embodiments, to evaluate whether an error exists in at least one of the registration or the contour determination, the at least one processor may be further configured to direct the system to perform additional operations including generating a comparison result between the ROI in the planning image volume and the ROI in the treatment image volume by comparing the first contour and the second contour, and evaluating whether the error exists in at least one of the registration or the contour determination based on the comparison result.

In some embodiments, the comparison result may relate to at least one of a volume difference between a volume of the ROI in the registered treatment image volume and a volume of the ROI in the registered planning image volume, or a surface area difference between a volume of the ROI in the registered treatment image volume and a volume of the ROI in the registered planning image volume.

In some embodiments, to generate the comparison result, the at least one processor may be further configured to direct the system to perform additional operations including determining a first intersection plane between a reference plane and the first contour, determining a second intersection plane between the reference plane and the second contour, and determining a similarity between the first intersection plane and the second intersection plane.

In some embodiments, the at least one processor may be further configured to direct the system to perform additional operations including identifying one or more reference regions in the registered planning image volume, and determining, based on the one or more reference regions, the reference plane.

In some embodiments, the one or more reference regions may relate to at least one of a target, an organ at risk, a rigid structure, or a region with a dose gradient higher than a threshold.

In some embodiments, to register the planning image volume and the treatment image volume with respect to a common coordinate system, the at least one processor may be further configured to direct the system to perform additional operations including reformatting at least one of the planning image volume or the treatment image volume so that the planning image volume and the treatment image volume are in a common voxel dimension, and registering the planning image volume and the treatment image volume in the common voxel dimension with respect to an isocenter of a radiation delivery device.

According to another aspect of the present disclosure, a method may be implemented on a computing device having at least one processor and at least one storage device for adaptive treatment planning. The method may include obtaining a planning image volume of a subject, a treatment image volume of the subject, and a first treatment plan related to the planning image volume of the subject, each of the planning image volume and the treatment image volume including an ROI of the subject. The method may also include registering the planning image volume and the treatment image volume with respect to a common coordinate system, and determining a first contour of the ROI in the registered planning image volume and a second contour of the ROI in the registered treatment image volume. The method may also include obtaining an evaluation result by evaluating whether an error exists in at least one of the registration or the contour determination based on the first contour and the second contour, and determining a second treatment plan with respect to the treatment image volume based on the evaluation result.

According to yet another aspect of the present disclosure, a non-transitory computer readable medium comprising a set of instructions for adaptive treatment planning is provided. When executed by at least one processor, the set of instructions direct the at least one processor to effectuate a method. The method may include obtaining a planning image volume of a subject, a treatment image volume of the subject, and a first treatment plan related to the planning image volume of the subject, each of the planning image volume and the treatment image volume including an ROI of the subject. The method may also include registering the planning image volume and the treatment image volume with respect to a common coordinate system, and determining a first contour of the ROI in the registered planning image volume and a second contour of the ROI in the registered treatment image volume. The method may also include obtaining an evaluation result by evaluating whether an error exists in at least one of the registration or the contour determination based on the first contour and the second contour, and determining a second treatment plan with respect to the treatment image volume based on the evaluation result.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
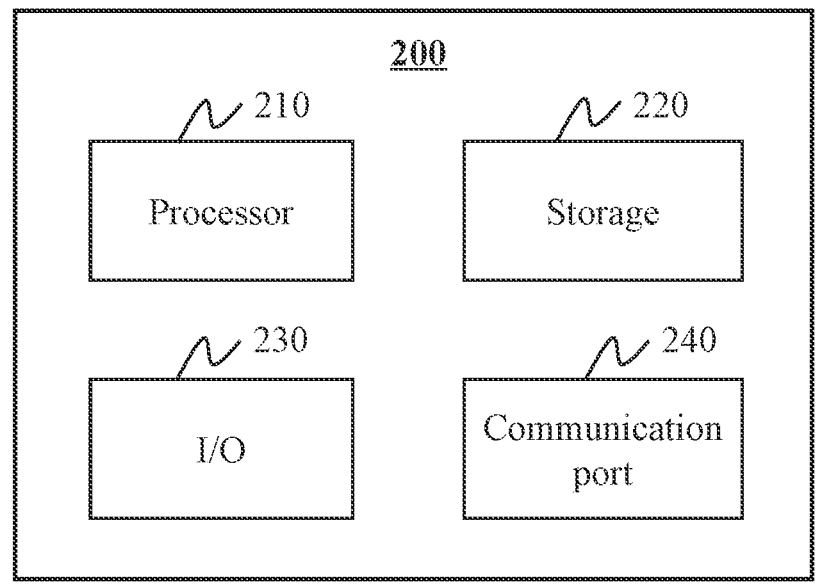
FIG. 2 is a schematic diagram illustrating an exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging and/or treatment, such as for disease diagnosis, treatment or research purposes. In some embodiments, the systems may include an RT system, a computed tomography (CT) system, an emission computed tomography (ECT) system, an X-ray photography system, a positron emission tomography (PET) system, or the like, or any combination thereof. For illustration purposes, the disclosure describes systems and methods for radiotherapy.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image (e.g., a planning image, or a treatment image, etc.) and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

The systems and methods provided in the present disclosure relate to adaptive treatment planning. The systems may perform the methods to obtain a planning image volume of a subject, a treatment image volume of the subject, and a first treatment plan related to the planning image volume of the subject. Each of the planning image volume and the treatment image volume may include a same region of interest (ROI) of the subject, such as a target and/or an organ at risk (OAR) of the subject. The systems may also perform the methods to register the planning image volume and the treatment image volume with respect to a common coordinate system. The systems may further perform the methods to determine a first contour of the ROI in the registered planning image volume and a second contour of the ROI in the registered treatment image volume, and obtain a first evaluation result by evaluating whether a first error exists in at least one of the registration or the contour determination based on the first contour and the second contour. The systems may perform the methods to determine a second treatment plan with respect to the treatment image volume based on the first evaluation result. For example, if the first evaluation result indicates that a first error exists in neither the registration nor the contour determination, the systems may perform the methods to determine whether the first treatment plan needs to be modified. In some embodiments, the second treatment plan may be the first treatment plan if the first treatment plan does not need to be modified, and the second treatment plan may be a modified treatment plan generated based on the second contour if the first treatment plan needs to be modified. Optionally, if the second treatment plan is the modified treatment plan, the systems may further perform the methods to evaluate whether a second error exists in the generation of the modified treatment plan.

According to some embodiments of the present disclosure, the registration, the contour determination, and/or the modified treatment plan may need to be verified using tools for identifying errors herein. This may improve the accuracy and/or reliability of the second treatment plan with respect to the treatment image volume, thereby improving the precision of treatment delivery, and/or reducing or avoiding unnecessary damages to the subject caused by inaccurate radiation delivery to the subject.

Figure 1:
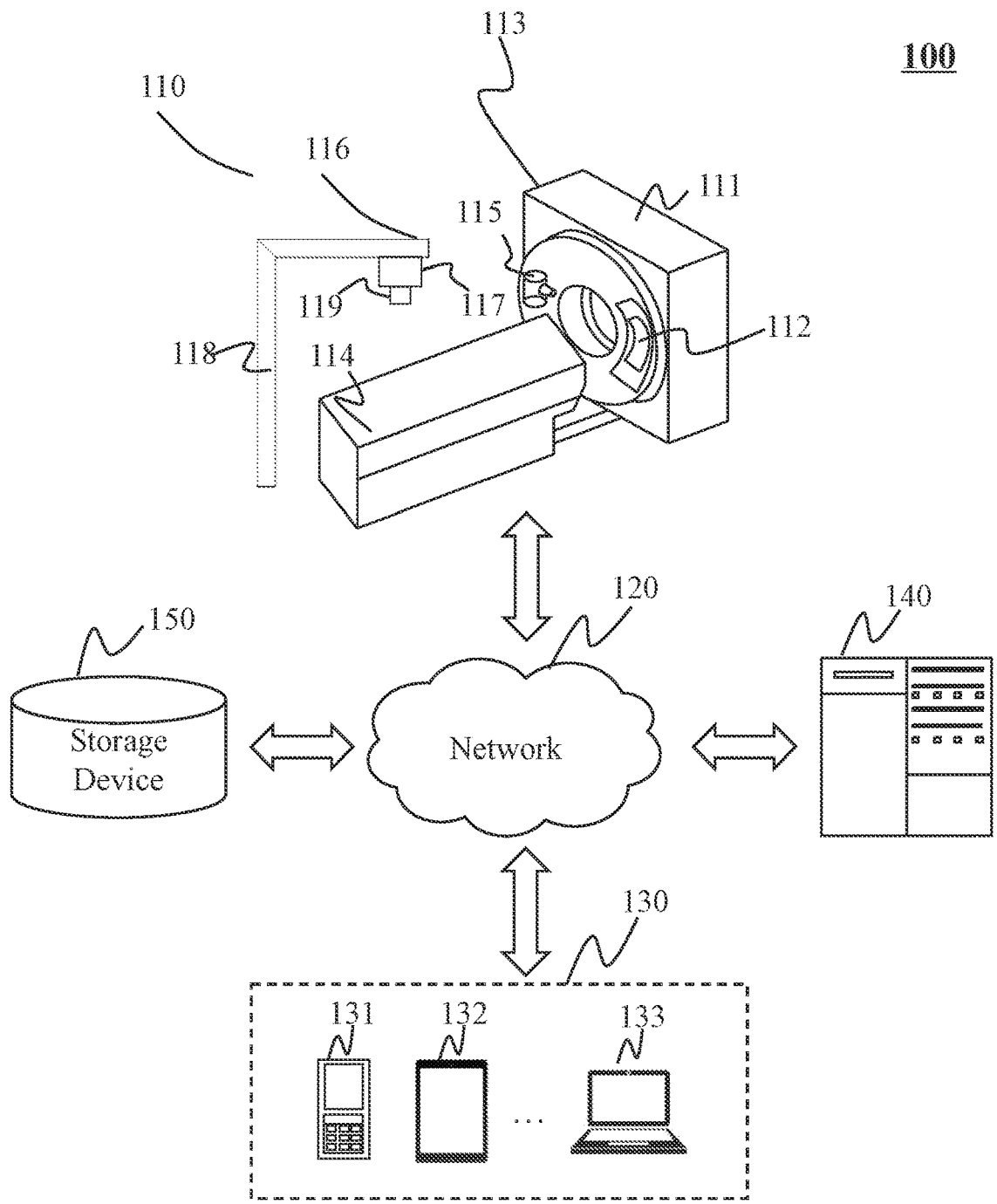
FIG. 1 is a schematic diagram illustrating an exemplary RT system according to some embodiments of the present disclosure.

FIG. 1 is a schematic diagram illustrating an exemplary RT system 100 according to some embodiments of the present disclosure. The RT system 100 may include a radiation delivery device 110, a network 120, a terminal 130, a processing device 140, and a storage device 150. In some embodiments, two or more components of the RT system 100 may be connected to and/or communicate with each other via a wireless connection (e.g., the network 120), a wired connection, or a combination thereof. The connection between the components of the RT system 100 may be variable. Merely by way of example, the radiation delivery device 110 may be connected to the processing device 140 through the network 120 or directly. As a further example, the storage device 150 may be connected to the processing device 140 through the network 120 or directly.

The radiation delivery device 110 may include an imaging component 113, a treatment component 116, a table 114, or the like. The imaging component 113 may be configured to acquire an image of a subject prior to radiotherapy treatment, during the radiotherapy treatment, and/or after the radiotherapy treatment. The subject may include any biological subject (e.g., a human being, an animal, a plant, or a portion thereof) and/or a non-biological subject (e.g., a phantom). For example, the imaging component may include a computed tomography (CT) device, an ultrasound imaging device, a fluoroscopy imaging device, a magnetic resonance imaging (MRI) device, a single photon emission computed tomography (SPECT) device, a positron emission tomography (PET) device, an X-ray imaging device, or the like, or any combination thereof.

In some embodiments, the imaging component 113 may include an imaging radiation source 115, a detector 112, a gantry 111, or the like. The imaging radiation source 115 and the detector 112 may be mounted on the gantry 111. The imaging radiation source 115 may emit radioactive rays to the subject. The detector 112 may detect radiation events (e.g., x-ray photons, gamma-ray photons) emitted from the imaging region of the imaging component 113. In some embodiments, the detector 112 may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The treatment component 116 may be configured to deliver radiation treatment to the subject. The treatment component 116 may include a treatment radiation source 117, a gantry 118, and a collimator 119. The treatment radiation source 117 may be configured to emit treatment radiations towards the subject. In some embodiments, the treatment radiation source 117 may include a linear accelerator (LINAC). The collimator 119 may be configured to control the shape of the treatment radiations generated by the treatment radiation source 117.

In some embodiments, the imaging component 113 may be spaced by a distance from the treatment component 116. In some embodiments, the gantry 111 of the imaging component 113 and the gantry 118 of the treatment component 116 may share an axis of rotation. The subject may be positioned in different positions on the table 114 for imaging and treatment. In some embodiments, the imaging radiation source 115 and the treatment radiation source 117 may be integrated as one radiation source to image and/or treat the subject. In some embodiments, the imaging component 113 and the treatment component 116 may share a same gantry. For example, the treatment radiation source 117 may be mounted on the gantry 111 of the imaging component 113. A subject may be placed on the table 114 for treatment and/or imaging.

The network 120 may include any suitable network that can facilitate the exchange of information and/or data for the RT system 100. In some embodiments, one or more components of the RT system 100 (e.g., the radiation delivery device 110, the terminal 130, the processing device 140, the storage device 150, etc.) may communicate information and/or data with one or more other components of the RT system 100 via the network 120. For example, the processing device 140 may obtain image data from the radiation delivery device 110 via the network 120. As another example, the processing device 140 may obtain user instructions from the terminal 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

Figure 3:
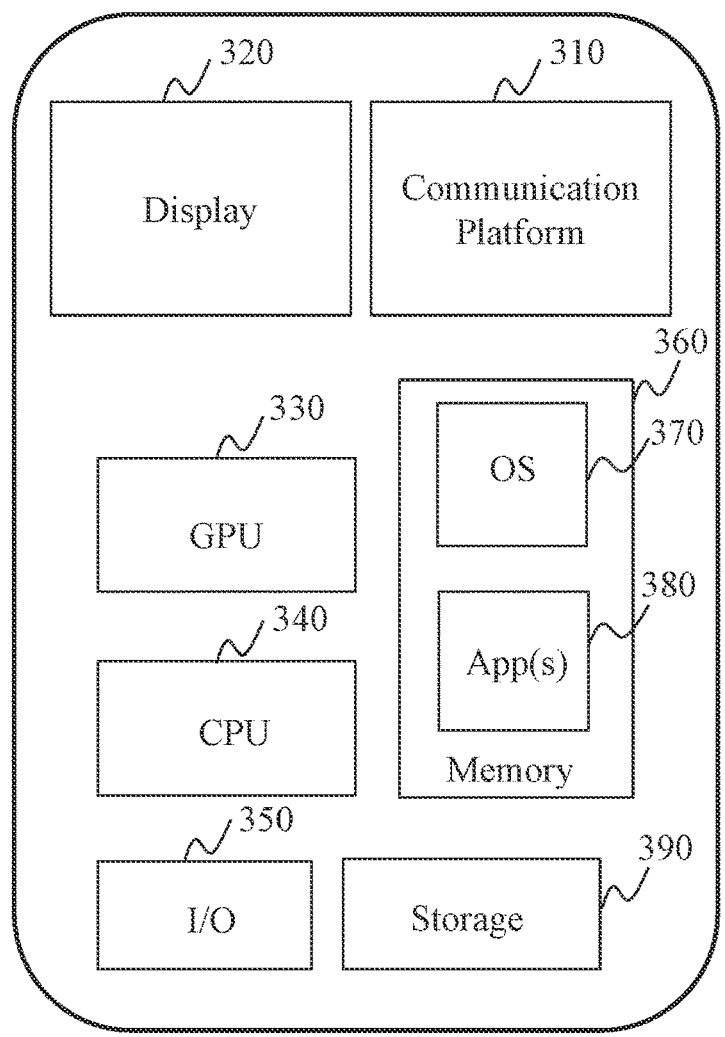
FIG. 3 is a schematic diagram illustrating hardware and/or software components of an exemplary mobile device according to some embodiments of the present disclosure.

The terminal 130 may enable user interaction between a user and the RT system 100. In some embodiments, the terminal 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal 130 may be part of the processing device 140.

The processing device 140 may process information obtained from the radiation delivery device 110, the terminal 130, and/or the storage device 150. In some embodiments, the processing device 140 may be a single server or a server group. The server group may be centralized or distributed. In some embodiments, the processing device 140 may be local or remote. For example, the processing device 140 may access information stored in the radiation delivery device 110, the terminal 130, and/or the storage device 150 via the network 120. As another example, the processing device 140 may be directly connected to the radiation delivery device 110, the terminal 130 and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the RT system 100 (e.g., the processing device 140, the terminal 130). One or more components of the RT system 100 may access the data and/or instructions stored in the storage device 150 via the network 120. In some embodiments, the storage device 150 may be directly connected to or communicate with one or more other components of the RT system 100 (e.g., the processing device 140, the terminal 130). In some embodiments, the storage device 150 may be part of the processing device 140.

FIG. 2 is a schematic diagram illustrating exemplary hardware and/or software components of a computing device 200 according to some embodiments of the present disclosure. The computing device 200 may be used to implement any component of the RT system 100 as described herein. For example, the processing device 140 and/or the terminal 130 may be implemented on the computing device 200, respectively, via its hardware, software program, firmware, or a combination thereof. Although only one such computing device is shown, for convenience, the computer functions relating to the RT system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the radiation delivery device 110, the terminal 130, the storage device 150, and/or any other component of the RT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data obtained from one or more components of the RT system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 to execute to check errors in replanning.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the radiation delivery device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 according to some embodiments of the present disclosure. In some embodiments, a terminal 130 and/or a processing device 140 may be implemented on a mobile device 300, respectively. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the RT system 100. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
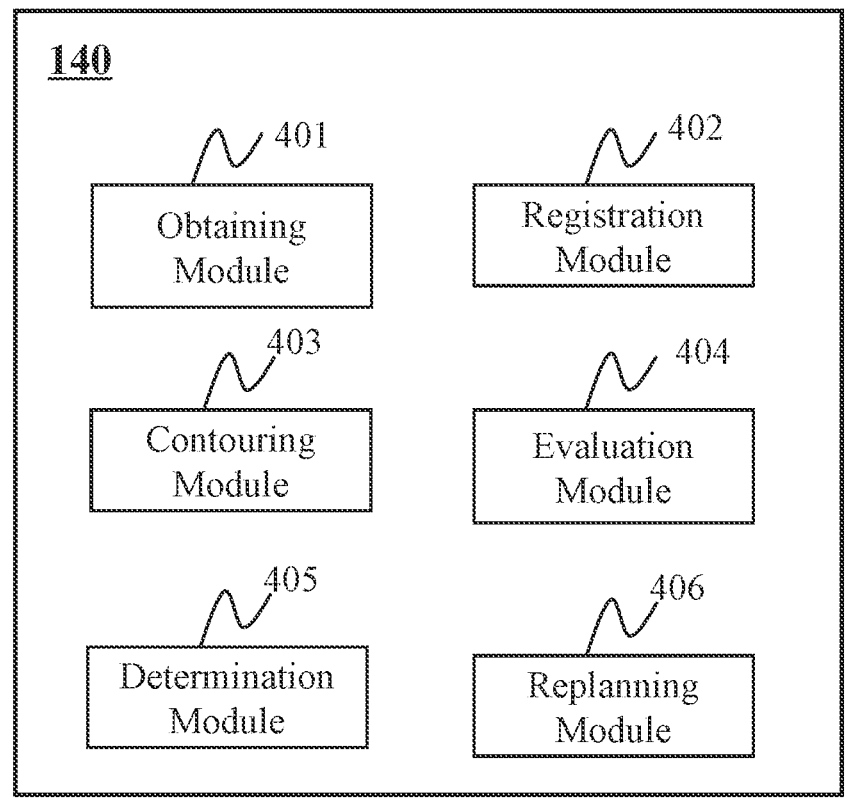
FIG. 4 is a block diagram illustrating an exemplary processing device according to some embodiments of the present disclosure.

FIG. 4 is a block diagram illustrating an exemplary processing device 140 according to some embodiments of the present disclosure. As shown in FIG. 4, the processing device 140 may include an obtaining module 401, a registration module 402, a contouring module 403, an evaluation module 404, a determination module 405, and a replanning module 406.

The obtaining module 401 may be configured to obtain information relating to the RT system 100. For example, the obtaining module 401 may obtain an image (e.g., a 2D image, a 3D image) of a subject from an image acquisition device (e.g., the imaging component 113) that captures the image or a storage device (e.g., the storage device 150) that stores the image. In some embodiments, the obtaining module 401 may obtain a planning image volume of the subject, a treatment image volume of the subject, and a first treatment plan related to the planning image volume of the subject. The planning image volume may refer to a 3D image or a set of 2D images of the subject according to which the first treatment plan is made. The first treatment plan may describe how a radiotherapy treatment is planned to be performed on the subject, more specifically, how one or more beams are delivered to the ROI of the subject during each treatment fraction over the course of treatment lasting a certain period of time. The treatment image volume may refer to a 3D image or a set of 2D images of the subject captured during the treatment procedure, for example, right before (e.g., minutes or hours before) a current treatment fraction starts or during the current treatment fraction.

The registration module 402 may be configured to perform image registration between a plurality of images. Merely by way of example, the registration module 402 may register the planning image volume and the treatment image volume to each other with respect to a common coordinate system. The registration may be performed based on any suitable image registration techniques including, for example, a voxel-based registration technique, a landmark-based registration technique, a segmentation-based registration technique, or the like, or a combination thereof. More descriptions regarding the registration between the planning image volume and the treatment image volume may be found elsewhere in the present disclosure. See, e.g., 502 and relevant descriptions thereof.

The contouring module 403 may be configured to determine a contour of an ROI (e.g., a certain organ, a target, an OAR) in an image. For example, the contouring module 403 may determine a first contour of the ROI in the registered planning image volume and a second contour of the ROI in the registered treatment image volume. In some embodiments, the contour of the ROI in the registered planning image volume and/or the registered treatment image volume may be determined manually, semi-automatically, or automatically. More descriptions regarding contour determination may be found elsewhere in the present disclosure. See, e.g., 503 and relevant descriptions thereof.

The evaluation module 404 may evaluate whether an error exists in a certain operation or process. For example, the evaluation module 404 may obtain a first evaluation result by evaluating whether a first error exists in at least one of the registration or the contour determination based on the first contour and the second contour. As another example, the evaluation module 404 may obtain a second evaluation result by evaluating whether a second error exists in the generation of a modified treatment plan. More descriptions regarding the generation of the first evaluation result and the second evaluation result may be found elsewhere in the present disclosure. See, e.g., 504 and 508 and relevant descriptions thereof.

The determination module 405 may determine a second treatment plan with respect to the treatment image volume based on the first evaluation result generated by the evaluation module 404. For example, if the first evaluation result indicates that a first error exists in neither the registration nor the contour determination, the determination module 405 may determine whether the first treatment plan needs to be modified. If the determination module 405 determines that the first treatment plan does not need to be modified, the determination module 405 may designate the first treatment plan as a second treatment plan with respect to the treatment image volume. More descriptions regarding the determination of the second treatment plane may be found elsewhere in the present disclosure. See, e.g., 505 to 509 and relevant descriptions thereof.

The replanning module 406 may be configured to modify the first treatment plan to generate a modified treatment plan if the determination module 405 determines that the first treatment plan needs to be modified. For example, the replanning module 406 may modify one or more parameters, such as the total dose and/or the dose distribution in the original first treatment plan based on the second contour and/or the comparison result between the first contour and the second contour, so that the first treatment plan may be modified to correspond to the new contour of the ROI to avoid or reduce an impact on healthy organs or tissue by radiation treatment. More descriptions regarding the generation of the modified treatment plan may be found elsewhere in the present disclosure. See, e.g., 507 and relevant descriptions thereof.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules and/or one or more modules described above may be omitted. Additionally or alternatively, two or more modules may be integrated into a single module and/or a module may be divided into two or more units. However, those variations and modifications also fall within the scope of the present disclosure.

Figure 5:
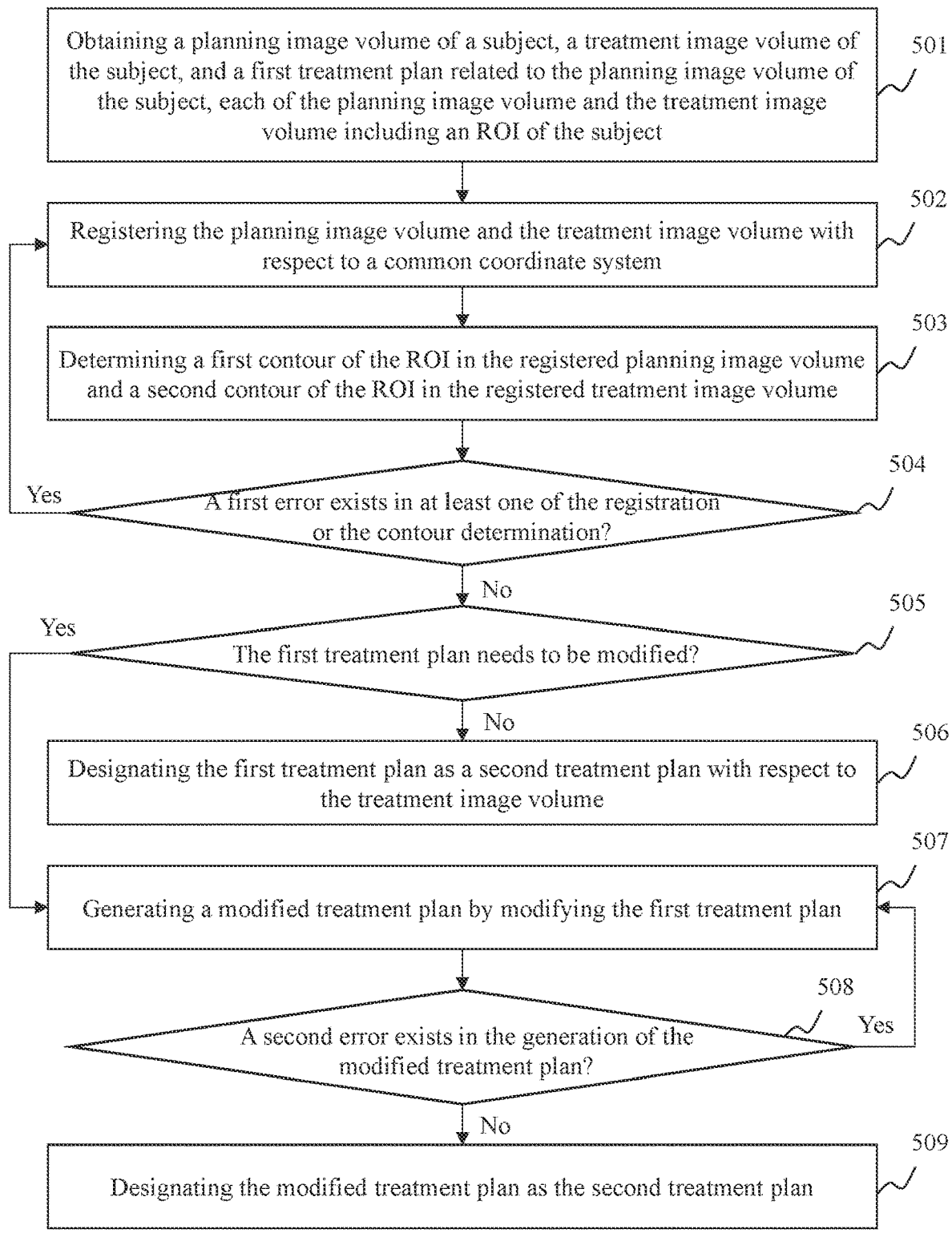
FIG. 5 is a flowchart illustrating an exemplary process for error checking in radiotherapy treatment replanning according to some embodiments of the present disclosure.

FIG. 5 is a flowchart illustrating an exemplary process for error checking in radiotherapy treatment replanning according to some embodiments of the present disclosure. In some embodiments, process 500 may be executed by the RT system 100. For example, the process 500 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 500.

In 501, the processing device 140 (e.g., the obtaining module 401) may obtain a planning image volume of a subject, a treatment image volume of the subject, and a first treatment plan related to the planning image volume of the subject. Each of the planning image volume and the treatment image volume may include a same region of interest (ROI) of the subject.

As used herein, the subject may refer to any biological subject and/or a non-biological subject. Exemplary biological subject may include a human being, an animal, a plant, or a portion thereof (e.g., a cell, a tissue, an organ, etc.). The ROI of the subject may include a region of the subject including at least part of malignant tissue (e.g., a tumor, a cancer-ridden organ, or a non-cancerous target of radiation therapy) and/or other tissue (e.g., a tissue surrounding the malignant tissue). For example, the ROI may include a target and/or one or more organs-at-risk (OAR). A target may refer to a certain anatomical structure that needs to be tracked or monitored during the radiotherapy treatment. For example, the target may be a tumor, an organ with a tumor, a tissue with a tumor, or any combination thereof, that needs to be treated by radiation. An OAR may include an organ or a portion thereof, and/or a tissue that is close to the target that is not intended to be subjected to radiation but under the risk of radiation damage due to its proximity to the target.

The planning image volume may refer to a 3D image or a set of 2D images of the subject according to which the first treatment plan is made. The first treatment plan may describe how a radiotherapy treatment is planned to be performed on the subject, more specifically, how one or more beams are delivered to the ROI of the subject during each treatment fraction over the course of treatment lasting a certain period of time, e.g., days. For example, the first treatment plan may provide a total dose (e.g., 0.1 Gy, 10 Gy, 50 Gy, 100 Gy, etc.) and a dose distribution in the ROI. In some embodiments, the first treatment plan may be a treatment plan determined at the beginning of the course of a radiotherapy treatment. Before the subject begins to receive the radiotherapy treatment (e.g., days or weeks before the treatment commences), the planning image volume of the subject may be acquired using an imaging device (e.g., the imaging component 113). The planning image volume may be used to identify the ROI (e.g., a target, an OAR) and/or and an external contour (e.g., skin) of the subject. The first treatment plan may be designed for the subject based on the planning image volume.

The treatment image volume may refer to a 3D image or a set of 2D images of the subject captured during the treatment procedure, for example, right before (e.g., minutes or hours before) a current treatment fraction starts or during the current treatment fraction. In some embodiments, the radiotherapy treatment of the subject may commence a couple of weeks after the subject is scanned for generating the planning image volume. The radiotherapy treatment may include a plurality of treatment fractions and last for a treatment period of multiple days (e.g., 2 to 5 weeks). As the treatment progresses, an anatomical change may take place within the ROI during the treatment period due to, for example, weight loss, growth, shrinkage, or disappearance of a tumor, and/or appearance of a new tumor, etc. Every time the subject comes for a treatment fraction, to ensure accurate positioning of the subject for the execution of the specific treatment fraction, the subject may be scanned for generating a treatment image volume. The anatomical change of the ROI may be identified by comparing the planning image volume and the treatment image volume.

In some embodiments, due to the anatomical change of the ROI, a treatment position of the subject in the current treatment fraction may need to be determined based on a registration between the planning image volume and the treatment image volume. An accurate delivery of the first treatment plan depends on that the subject is positioned properly so that the target of the subject is positioned properly to receive radiation whose delivery is specified in the first treatment plan. Thus, the treatment position determined based on the registration between the planning image volume and the treatment image volume may improve the precision and accuracy of treatment delivery.

In some embodiments, if the amount of change of the ROI exceeds a threshold, the original first treatment plan may need to be modified in order to reduce toxicity to portions of the subject by unintended radiation, and improve targeting of the target and overall outcome of the treatment. The modified treatment plan may be performed with respect to the current treatment fraction or a subsequent treatment fraction. In some embodiments, the amount of the change of the ROI may be measured by a change in one or more features of the ROI including, e.g., the size, the position, the volume, the shape, or the like, of the ROI. In some embodiments, the amount of the change of the ROI may be determined based on the contours of the ROI in the registered planning image volume and the registered treatment image volume. For example, by comparing a contour of a tumor in the planning image volume and a contour of the tumor in the treatment image volume, a volume change of the tumor may be determined. A radiation dose delivered to the tumor may be determined based on the volume change of the tumor, and accordingly the first treatment plan may be modified to correspond to the new volume of the tumor without delivering radiation to an OAR.

In 502, the processing device 140 (e.g., the registration module 402) may register the planning image volume and the treatment image volume to each other with respect to a common coordinate system.

The registration may be performed based on any suitable image registration techniques including, for example, a voxel-based registration technique, a landmark-based registration technique, a segmentation-based registration technique, or the like, or a combination thereof. In some embodiments, the registration between the planning image volume and the treatment image volume may be a rigid registration.

The common coordinate system may be any suitable coordinate system. The planning image volume and the treatment image volume may be registered to each other so that they are both represented in the common coordinate system. For example, originally the planning image volume and the treatment image volume may be represented in a coordinate system A and a coordinate system B, respectively. The coordinate systems A and B may be a same coordinate system or different coordinate systems. The planning image volume and the treatment image volume may need to be transformed (or registered) to a common coordinate system (e.g., the coordinate system A or B, or another coordinate system). In some embodiments, the planning image volume and the treatment image volume may be registered to share a common isocenter. For example, the isocenter of the planning image volume (e.g., a central point of a target in the planning image volume) and the isocenter of the treatment image volume (e.g., a central point of the target in the treatment image volume) may coincide so that the planning image volume and the treatment image volume share a common isocenter. Optionally, the common isocenter may coincide with the LINAC isocenter of the radiation delivery device 110. In some embodiments, a registration matrix between the planning image volume and the treatment image volume may be determined in the registration. The registration matrix may represent a transformation relationship between the treatment image volume and the planning image volume. For example, if a voxel of a certain physical point in the planning image volume has a coordinate C in the coordinate system A and a voxel of the same physical point in the treatment image volume has a coordinate D in the coordinate system B, the registration matrix may record a transformation relationship between the coordinates C and D.

In some embodiments, during the registration, the planning image volume and/or the treatment image volume may be reformatted so that the planning image volume and the treatment image volume are expressed using a common voxel dimension. For example, the reformatted images using a common voxel dimension may be 3D images that have a same voxel size. In this way, a first portion in the planning image volume and a second portion in the treatment image volume that correspond to a same physical portion of the subject (e.g., a same target, a same OAR) may be superimposed for display in the common voxel dimension. In some embodiments, the reformatting of the planning image volume and the treatment image volume may be performed at the same time with, before, or after the isocenter alignment of the planning image volume and the treatment image volume.

In 503, the processing device 140 (e.g., the contouring module 403) may determine a first contour of the ROI in the registered planning image volume and a second contour of the ROI in the registered treatment image volume.

As described in connection with operation 501, the ROI may include a target and/or an OAR of the subject. The first contour may refer to the contour of the ROI in the registered planning image volume, and the second contour may refer to the contour of the ROI in the registered treatment image volume. In some embodiments, the contour of the ROI in the registered planning image volume and/or the registered treatment image volume may be determined manually, semi-automatically, or automatically. In an automatic approach, the contour of the ROI may be identified from an image automatically by a computing device (e.g., the computing device 200 as illustrated in FIG. 2) without user intervention. For example, the contour of the ROI may be segmented from an image automatically according to a contour detection algorithm, such as a Sobel edge detection algorithm, a Canny edge detection algorithm, a phase congruency-based algorithm, or the like, or a combination thereof. In a semi-automatic approach, the contour of the ROI may be identified from an image by a computing device (e.g., the computing device 200 as illustrated in FIG. 2) with user intervention. For example, the contour identification may be performed by the computing device based on a contour detection algorithm in combination with information provided by a user. Exemplary user intervention in a semi-automatic approach for the contour detection may include providing a parameter relating to the contour detection algorithm, providing a position parameter relating to the ROI, making an adjustment to or confirming a preliminary contour detection performed by the computing device, providing instructions to cause the computing device to repeat or redo the contour detection, etc. In a manual approach, the contour of the ROI may be identified from an image according to an instruction provided by a user. For example, via a user interface implemented on, e.g., a terminal 130 or a mobile device 300 as illustrated in FIG. 3, a user may mark the first contour in the registered planning image volume and/or the second contour in the registered treatment image volume.

In some embodiments, a contour of the ROI in the planning image volume may be determined in advance and stored in a storage device (e.g., the storage device 150, the storage 220, an external source). The processing device 140 may directly retrieve the contour of the ROI in the planning image volume from the storage device. Optionally, the obtained contour may be used as prior information to determine the second contour of the ROI in the registered treatment image volume using a technique, such as a deformable image registration (DIR) technique, or an automated segmentation (AS) technique, or the like, or any combination thereof. Merely by way of example, the second contour of the ROI in the registered treatment image volume may be determined based on the DIR technique. As described above, after the treatment image volume and the planning image volume are registered, a registration matrix recording a transformation relationship between the planning image volume and the treatment image volume may be generated. Thus, the second contour of the ROI in the registered treatment image volume may be determined based on the contour of the ROI in the planning image volume and the registration matrix. As another example, the second contour of the ROI in the treatment image volume may be determined based on the AS technique. Merely by way of example, a reference histogram and/or a reference gray level of an area within the contour of the ROI in the planning image volume may be determined. The registered treatment image volume may be segmented based on the reference histogram and/or the reference gray level. Then the second contour of the ROI in the treatment image volume may be determined based on the segmented registered treatment image volume.

As aforementioned, the treatment position of the subject may be determined based on the registration between the planning image volume and the treatment image volume. Additionally or alternatively, the first contour and the second contour of the ROI may serve as a basis of replanning. The registration between the planning image volume and the treatment image volume and/or the contour identification or determination need to be sufficiently accurate to be used as input for replanning. Therefore, it is desirable to provide effective tools for evaluating the accuracy of the registration discussed in 502 and/or the contour determination discussed in 503, so as to improve the replanning accuracy.

In 504, the processing device 140 (e.g., the evaluation module 404) may obtain a first evaluation result by evaluating whether a first error exists in at least one of the registration or the contour determination based on the first contour and the second contour.

In some embodiments, the processing device 140 may generate a comparison result between the ROI in the planning image volume and the ROI in the treatment image volume based on the first contour and the second contour. The processing device 140 may further evaluate whether a first error exists in at least one of the registration or the contour determination based on the comparison result.

For example, the comparison result may relate to a volume difference between a volume of the ROI in the registered treatment image volume and a volume of the ROI in the registered planning image volume. Additionally or alternatively, the comparison result may relate to a surface area difference between a surface area of the ROI in the registered treatment image volume and a surface area of the ROI in the registered planning image volume. The volume and/or the surface area of the ROI in the registered planning image volume may be determined based on the first contour of the ROI in the registered planning image volume. The volume and/or the surface area of the ROI in the registered treatment image volume may be determined based on the second contour of the ROI in the registered treatment image volume.

The existence of a first error may be verified based on the volume difference and/or surface area difference. For example, if the volume difference exceeds a first threshold of volume difference, a warning may be raised as the volume difference may indicate that an error (e.g., a contouring error and/or a registration error) may exist causing a significant change in the volume of the ROI in at least one of the registered planning image volume or the registered treatment image volume, or that the determined volume difference accurately reflects a genuine change in the anatomy of the target and/or OAR in the subject corresponding to the ROI. Similarly, if the surface area difference exceeds a second threshold of surface area difference, a warning may be raised as the surface area difference may indicate that an error (e.g., a contouring error and/or a registration error) may exist causing a significant change in the surface area of the ROI in at least one of the registered planning image volume or the registered treatment image volume, or that the determined surface area change accurately reflects a genuine change in the anatomy of the target and/or OAR in the subject corresponding to the ROI.

In some embodiments, if the volume difference exceeds the first threshold and/or the surface area difference exceeds the second threshold, the processing device 140 may transmit a warning regarding the volume difference and/or the surface area difference to a user. The user may verify whether the volume difference and/or the surface area difference are caused by an error in registration, an error in the contour determination, or a genuine change in the anatomy of the target and/or OAR in the subject that corresponds to the ROI. Based on the user's response, the processing device 140 may determine whether a first error exists in the registration and/or the contour determination. In some embodiments, if the volume difference exceeds the first threshold and/or the surface area difference exceeds the second threshold, the processing device 140 may need to verify the accuracy of the registration algorithm used in the registration between the planning image volume and the treatment image volume. For example, a contour of a boney structure may be determined in each of the planning image volume and the treatment image volume manually by a user or automatically by the processing device 140. The contours of the boney structure may be registered using the registration algorithm. If the registration result indicates that the overlap between the contours exceeds a threshold level, the processing device 140 may determine that the registration algorithm has a high accuracy, and the volume difference and/or the surface area difference may be caused by the anatomical change of the target and/or OAR in the subject.

In some embodiments, the comparison result may relate to a first intersection plane between a reference plane and the first contour and a second intersection plane between the reference plane and the second contour. The reference plane may be any plane, such as an axial plane, a coronal plane, a sagittal plane, or an oblique plane that passes through an overlapping volume between the registered planning image volume and the registered treatment image volume. An oblique plane may include a beam's eyes view (BEV) plane that passes through the isocenter of the radiation delivery device 110. In some embodiments, the processing device

140 may determine the first intersection plane between the reference plane and the first contour of the ROI in the registered planning image volume. The processing device 140 may also determine the second intersection plane between the reference plane and the second contour of the ROI in the registered treatment image volume.

Figure 6:
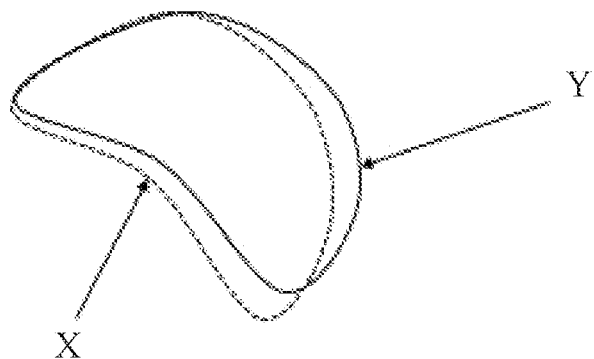
FIG. 6 is a schematic diagram illustrating exemplary intersection planes according to some embodiments of the present disclosure.

The processing device 140 may generate the comparison result based on the first intersection plane and the second intersection plane. For example, the comparison result may relate to a degree of similarity (or referred to as a similarity for brevity) between the first intersection plane and the second intersection plane. For illustration purposes, FIG. 6 illustrates exemplary intersection planes according to some embodiments of the present disclosure. As shown in FIG. 6, X represents a first intersection plane between a certain reference plane and the first contour of the ROI in the registered planning image volume, and Y represents a second intersection plane between the certain reference plane and the second contour of the ROI in the registered treatment image volume. In some embodiments, the similarity between the X (i.e., the first intersection plane) and Y (i.e., the second intersection plane) may be assessed according to $$\frac{2|X \cap Y|}{|X|+|Y|}.$$

The existence of a first error may be verified according to the similarity. For example, if the similarity between X and Y is less than a third threshold of similarity, the processing device 140 may determine that a first error (e.g., a contouring error or a registration error) occurs on the certain reference plane. Optionally, the processing device 140 may generate a notification regarding the dissimilarity between X and Y and transmit the notification to a user for verification. The processing device 140 may determine whether a first error exists according to a response of the user regarding the dissimilarity.

Theoretically, there exists an infinite number of reference planes through the overlapping volume between the registered planning image volume and registered treatment image volume, and it may be inefficient to search a large subset of these reference planes and/or specify corresponding thresholds of similarity suitable for uncovering the error in the registration or contour determination. In order to efficiently identify a specific reference plane that may reveal a possible similarity between X and Y lower than the third threshold, the processing device 140 may identify one or more reference regions in the registered planning image volume, and determine the specific reference plane based on the one or more reference regions. Each reference region may relate to a target, an OAR, a rigid structure, a region with a dose gradient higher than a threshold, or the like, or any combination thereof.

In some embodiments, the reference region(s) may include a target and/or an OAR close to the target. For example, a target that is prone to deformation and/or one or more OARs that are close to the target and may get adversely affected due to displacement or deformation may be identified as the reference region(s). For cancer in a specific region of the subject, there may be one or more specific critical OARs that need to be identified as reference region(s) and examined carefully by, e.g., being taken into consideration in determining the comparison result. Merely by way of example, for gynecological cancer, the cervix and uterus may be identified as reference regions because cervix and uterus movement is significantly related with bladder and rectum filling and may need to be carefully examined for verifying the registration and/or contouring accuracy. For prostate cancer, at least one of the prostate, the seminal vesicle, the rectum, or bladder the may be identified as reference region(s) to be examined carefully, and a fixed protocol (e.g., full/empty bladder, empty rectum using laxative) may be followed in each treatment fraction. For a head and neck cancer, at least one of the parotid, the salivary gland, the optical nerve, or the spinal cord may be identified as reference regions. In addition, there is one or more cancer lesion, in each of which there is a known shared anatomical boundary between organs (e.g., bowel and bladder, rectum and prostate, bladder and vagina). Such an anatomical boundary may be prioritized for inspection and identified as a reference region. Moreover, an OAR expected to expand and contract may also be identified as a reference region. Once the target and/or the OAR(s) are identified, the processing device 140 may determine a reference plane within a region enclosing the target and/or the OAR(s). For example, a plurality of axial (or coronal or sagittal) planes with a regular interval between adjacent planes enclosing the span of the target and/or the OAR(s) may be determined for further examination. As another example, the processing device 140 may determine a set of gantry angles of the gantry 118 at which radiations are planned to be delivered (or a portion of the gantry angles) according to the first treatment plan. For each of the gantry angles, a plurality of reference planes within the region enclosing the target and/or the OAR(S) that have a regular interval between adjacent reference planes and are orthogonal to the beam central axis from the gantry angle may be determined for further examination.

In some embodiments, the reference region(s) may include a rigid structure, such as a bone. The contour of a rigid structure in the registered planning image volume and the registered treatment image volume may be expected to have a high similarity (e.g., a similarity higher than a third threshold with respect to the rigid structure). The processing device 140 may determine a reference plane passing through the rigid structure to identify errors in registration and/or contouring. For example, a plurality of axial planes that have a regular interval between adjacent axial planes passing through the rigid structure may be determined as reference planes for further examination.

In some embodiments, the reference region(s) may include a region with a high dose gradient (e.g., a dose gradient higher than a threshold gradient). A dose gradient of a region may be measured by, for example, a difference between the maximum dose and the minimum dose, a variation of doses in the region. The dose gradient may be determined based on the first treatment plan. If a significant deformation occurs in a region with a high dose gradient, there may be a potential for a serious error, and thus the region may be determined as a reference region.

In some embodiments, for different ROIs (e.g., different organs), the values of a threshold (e.g., the first threshold of volume difference, the second threshold of surface area difference, the third threshold) may be different. For example, the value of the threshold for a soft organ (e.g., the bladder, the rectum) may be larger than that for a solid organ (e.g., the heart, the liver). The value of the threshold for a solid organ may be larger than that for a rigid organ (e.g., bone). As used herein, a soft organ may refer to an organ that mainly includes tendon, ligament, fascia, skin, fibrous tissue, fat, and synovial membranes, muscle, and/or other soft tissue. A solid organ may refer to an organ that has a firm tissue consistency and is neither hollow nor liquid (such as blood). A rigid organ may include a bone. The volume of a soft organ may be expected to change over time, but the volume of a solid organ may be expected to change less than a soft organ, and the volume of a bone may barely change. In some embodiments, the value of a threshold may be set as a default setting of the RT system 100 or be inputted by a user. Alternatively, the value of a threshold may be determined by, for example, the processing device 140. For example, the value of the first threshold of a specific organ may be determined based on HU ranges of different organs if the planning image volume or the treatment image volume are acquired using CT. Merely by way of example, a specific ROI may include a set of voxels that have values in the HU range for bone. The specific ROI may be considered as bone, and the value of the first threshold of the specific ROI may be equal to or substantially equal to 0.

In some embodiments, in response to a first evaluation result that a first error exists in the registration and/or contour determination, the processing device 140 may generate a notification (e.g., an image notification, a sound notification, etc.) regarding the first error and transmit the notification to a terminal device (e.g., the terminal 130). Additionally or alternatively, the processing device 140 may perform 502 to 504 again or modify the registration result and/or the contour determination result until the first evaluation result indicates that there is no first error.

Based on the first evaluation result, the processing device 140 may determine a second treatment plan with respect to the treatment image volume. The second treatment plan may be performed on the subject in the current treatment fraction or a subsequent treatment fraction. In some embodiments, the first evaluation result may indicate that a first error exists in neither the registration nor the contour determination, the processing device 140 may obtain a determination result by determining whether the first treatment plan needs to be modified. The processing device 140 may also determine the second treatment plan based on the first evaluation result and the determination result. In some embodiments, if the first evaluation result indicates that a first error exists in neither the registration nor the contour determination, the process 500 may proceed to 505, in which the processing device 140 (e.g., the determination module 405) may obtain the determination result by determining whether the first treatment plan needs to be modified. For example, the processing device 140 may determine whether the difference between the ROI in the registered planning image volume and the ROI in the registered treatment image volume exceeds a threshold difference. The difference may include a volume difference, a shape difference, a position difference, or the like, or any combination thereof. In some embodiments, the difference may be determined based on the first contour and the second contour, for example, based on the first comparison result as described in connection with 504. If the difference does not exceed the threshold difference, the processing device 140 may generate a determination result including that the first treatment plan does not need to be modified, and proceed to 506. In 506, the processing device 140 (e.g., the determination module 405) may designate the first treatment plan as a second treatment plan with respect to the treatment image volume.

If it is determined that the difference exceeds the threshold difference, the processing device 140 may generate a determination result including that the first treatment plan needs to be modified, and proceed to 507. In 507, the processing device 140 (e.g., the replanning module 406) may modify the first treatment plan to generate a modified treatment plan based on the second contour of the ROI in the registered treatment image volume.

In some embodiments, the processing device 140 may modify one or more parameters, such as the total dose and/or the dose distribution in the original first treatment plan based on the second contour and/or the comparison result between the first contour and the second contour, so that the first treatment plan may be modified to correspond to the new contour of the ROI to avoid or reduce an impact on healthy organs or tissue by radiation treatment.

In some embodiments, after the modified treatment plan is generated, the processing device 140 (e.g., the determination module 405) may designate the modified treatment plan as the second treatment plan directly. Alternatively, the processing device 140 e.g., the evaluation module 404) perform 508 to obtain a second evaluation result by evaluating whether a second error exists in the generation of the modified treatment plan.

In some embodiments, the processing device 140 may determine one or more characteristic spots in the registered treatment image volume based on the modified treatment plan, and evaluate whether a second error exists in the generation of the modified treatment plan based on the characteristic spot(s) in the registered treatment image volume. A characteristic spot may include a hot-spot, a potential hot-spot, a cold-spot, a potential cold-spot, or the like, or any combination thereof. A hot-spot may include one or more voxels corresponding to a portion of the subject that may receive a planned radiation dose higher than an expected maximum dose according to the modified treatment plan. A cold-spot may include one or more voxels corresponding to a portion of the subject that may receive a planned radiation dose lower than an expected minimum dose according to the modified treatment plan. For example, if a planned dose D(v) of a voxel v in the modified treatment plan is greater than the expected maximum dose (e.g., a sum of a prescribed maximum dose $D_{max}$ and a dose tolerance $\in_D$ of the voxel v), the voxel v may be regarded as being located in a hot-spot. If the planned dose D(v) of the voxel v in the modified treatment plan is smaller than the expected minimum dose (e.g., a difference between a prescribed minimum dose $D_{max}$ and the dose tolerance $\in_D$), the voxel v may be regarded as being located in a cold-spot. A potential hot-spot may include one or more voxels that are close to voxel(s) in a hot-spot. A potential cold-spot may include one or more voxels that are close to voxel(s) in a cold-spot. For example, if a distance between a voxel v' and a voxel in a hot-spot is shorter than a distance tolerance $\in$, the voxel v' may be regarded as being located in a potential hot-spot. If a distance between the voxel v' and a voxel in a cold-spot is shorter than the distance tolerance $\in$, the voxel v' may be regarded as being located in a potential cold-spot. In some occasions, a voxel in a potential hot-spot may enter a hot-spot and/or a voxel in a potential cold-spot may enter a cold spot during treatment due to an anatomical displacement and/or deformation. Thus, voxels in potential hot-spots and/or potential cold-spot may need to be considered in verifying the modified treatment plan.

In some embodiments, the processing device 140 may analyze each voxel in the registered treatment image volume (or in the ROI of the registered treatment image volume) to identify the characteristic spot(s) in the registered treatment image volume. Alternatively, in order to quickly identify the characteristic spot(s) in the registered treatment image volume, the processing device 140 may obtain or determine characteristic spot(s) in the registered planning image volume according to the original first treatment plan, and determine the characteristic spots in the registered treatment image volume based on the characteristic spot(s) in the registered planning image volume. For example, the characteristic spot(s) in the registered planning image volume may be determined in advance and stored in a storage device, and the processing device 140 may retrieve information relating to the characteristic spot(s) in the registered planning image volume, and determine the characteristic spot(s) in the registered planning image volume based on the retrieved information. In some embodiments, one or more planes (e.g., axial planes) passing through one or more characteristic spots in the registered planning image volume may be identified in an overlapping volume between the registered planning image volume and the registered treatment image volume. The processing device 140 may identify one or more characteristic spots in each identified plane in the registered treatment image volume.

After the characteristic spot(s) are identified in the registered treatment image volume, the processing device 140 may generate the second evaluation result regarding the modified treatment plan based on the characteristic spot(s). For example, the processing device 140 may determine whether the characteristic spot(s) satisfy a dose constraint. Exemplary dose constraints may be that a volume of a cold-spot is less than a certain percentage (e.g., 1%) of the volume of a planning target volume (PTV), that the radiation dose planned to delivery to a cold spot is not below a certain percentage (e.g., 5%) of a prescribed dose (e.g., a dose prescribed by a radiation oncologist), and that a cold spot may be located at a periphery of the PTV but not within a clinic target volume (CTV). As used herein, a CTV may refer to a tissue volume that includes a clinically malignant tissue and/or a subclinical malignant tissue at a certain probability level. The term "subclinical malignant tissue" may refer to malignant tissue that has little or no signs or symptoms that are detectable by clinical detection. A PTV may refer to a region surrounding the CTV with an additional margin that allows for variations and/or uncertainties in planning and/or treatment relative to the CTV. Other exemplary dose constraints may be that a volume of a hot-spot is within a certain range (e.g., 15-20%) of the volume of the PTV, that the volume of overdosing hot-spots is less than a certain percentage of the volume of the PTV, that a hot spot may be located within the CTV or a gross target volume (GTV) but not on the periphery of the PTV. As used herein, a GTV may refer to a tissue volume that includes a clinically malignant tissue (e.g., a tumor). An overdosing hot-spot may refer to a hotspot with a planned radiation dose higher than a certain level, such as 110% or 115 of a prescribed dose. For example, a dose constraint may be that the volume of overdosing hot-spots with planned radiation dose higher than a certain level (e.g., 110%) of the prescribed dose is within a range (e.g., smaller than 15%) of the volume of the PTV or that the volume of overdosing hot-spots with planned radiation dose higher than a certain level (e.g., 115%) of the prescribed dose is within a range (e.g., smaller than 1%) of the volume of the PTV. Specific ranges and threshold levels of radiation doses exemplified above are provided for illustration purposes and not intended to be limiting. These ranges and threshold levels of radiation doses may be specified by a user (e.g., a physician, an oncologist) or determined by the RT system 100 according to certain rules for individual subjects.

In some embodiments, if it is determined that the characteristic spot(s) in the registered treatment image volume satisfies the dose constraint, the processing device 140 may generate a second evaluation result including that there is no second error in the generation of the modified treatment plan. In response to the second evaluation result that there is no second error in the generation of the modified treatment plan, the process 500 may proceed to 509. In 509, the processing device 140 (e.g., the determination module 405) may designate the modified treatment plan as the second treatment plan with respect to the treatment image volume. The second treatment plan may be performed on the subject in the current treatment fraction or a subsequent treatment fraction.

If it is determined that the characteristic spot(s) in the registered treatment image volume do not satisfy the dose constraint, the processing device 140 may generate a second evaluation result including that a second error exists in the generation of the modified treatment plan. In response to the second evaluation result that the second error exists in the generation of the modified treatment plan, the process 500 may proceed to 507 again to generate a modified treatment plan by modifying the original first treatment plan, or the processing device 140 may further modify the modified treatment plan until the second evaluation result indicates that there is no second error in the generation of the modified treatment plan. This may avoid replanning error and improve replanning accuracy.

Optionally, the processing device 140 may generate a notification (e.g., an image notification, a sound notification, etc.) regarding the second error and transmit the notification to a terminal device (e.g., the terminal 130). In addition, the processing device 140 may identify plane(s) passing through abnormal characteristic spot (e.g., a characteristic spot does not meet the dose constraint) and display the dose distribution in the plane(s) to a user. The dose distribution in a plane may be displayed in various ways, such as in a direct display manner (e.g., an Iso-dose curve, an Iso-dose surface, a color wash image of dose distribution) and/or an indirect display manner (e.g., a dose volume histogram). Compared with displaying the dose distribution in the whole registered treatment image volume, displaying the dose distribution in the plane(s) with errors may be more efficient for the user to make a faster and more comprehensive decision about the quality of the modified treatment plan.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. In some embodiments, operation 502 may be omitted. In some embodiments, one or more of operations 503 to 509 may be performed based on the original planning image volume and/or the original treatment image volume. The terms "registered planning image volume" and "planning image volume" may be used interchangeably, and the terms "registered treatment image volume" and "treatment image volume" may be used interchangeably.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification is provided for illustration purposes and modified according to different situations. For example, a classification condition that "a probability value is greater than the threshold value" may further include or exclude a condition that "the probability value is equal to the threshold value."

We claim:

1. A system, comprising:
    at least one storage device including a set of instructions for adaptive treatment planning; and
    at least one processor configured to communicate with the at least one storage device, wherein when executing the set of instructions, the at least one processor is configured to direct the system to perform operations including:

obtaining a planning image volume of a subject, a treatment image volume of the subject, and a first treatment plan related to the planning image volume of the subject;

obtaining a determination result by determining, based on the planning image volume and the treatment image volume, whether the first treatment plan needs to be modified, in response to the determination result that the first treatment plan needs to be modified, generating a modified treatment plan by modifying the first treatment plan;

obtaining an evaluation result by evaluating whether an error exists in the generation of the modified treatment plan by:

registering the planning image volume and the treatment image volume with respect to a common coordinate system;

identifying one or more planes in an overlapping volume between the registered planning image volume and the registered treatment image volume, the one or more planes passing through one or more characteristic spots in the registered planning image volume; and obtaining the evaluation result based on one or more characteristic spots on the one or more planes in the registered treatment image volume; and generating, based on the evaluation result, a second treatment plan with respect to the treatment image volume.

2. The system of claim 1, wherein the generating, based on the evaluation result, a second treatment plan with respect to the treatment image volume comprises:

in response to the evaluation result that error exists in the generation of the modified treatment plan, generating the second treatment plan by further modifying the modified treatment plan or modifying the first treatment plan; or in response to the evaluation result that no error exists in the generation of the modified treatment plan, designating the modified treatment plan as the second treatment plan.

3. The system of claim 1, wherein the obtaining a determination result by determining, based on the planning image volume and the treatment image volume, whether the first treatment plan needs to be modified comprises:

determining a first contour of an ROI in the registered planning image volume and a second contour of the ROI in the registered treatment image volume; and determining, based on the first contour and the second contour, whether the first treatment plan needs to be modified.

4. The system of claim 3, wherein the operations further comprise:

generating a comparison result between the ROI in the planning image volume and the ROI in the treatment image volume by comparing the first contour and the second contour; and evaluating, based on the comparison result, whether a second error exists in at least one of the registration or the contour determination.

5. The system of claim 4, wherein the comparison result relates to at least one of:

a volume difference between a volume of the ROI in the registered treatment image volume and a volume of the ROI in the registered planning image volume, or a surface area difference between a volume of the ROI in the registered treatment image volume and a volume of the ROI in the registered planning image volume.

6. The system of claim 4, wherein the generating the comparison result comprises:

determining a first intersection plane between a reference plane and the first contour;

determining a second intersection plane between the reference plane and the second contour; and determining a similarity between the first intersection plane and the second intersection plane.

7. The system of claim 6 wherein the operations further comprise:

identifying one or more reference regions in the registered planning image volume; and determining, based on the one or more reference regions, the reference plane.

8. The system of claim 7, wherein the one or more reference regions relate to at least one of a target, an organ at risk, a rigid structure, or a region with a dose gradient higher than a threshold.

9. The system of claim 1, wherein the registering the planning image volume and the treatment image volume with respect to a common coordinate system comprises:

reformatting at least one of the planning image volume or the treatment image volume so that the planning image volume and the treatment image volume are in a common voxel dimension; and registering the planning image volume and the treatment image volume in the common voxel dimension with respect to an isocenter of a radiation delivery device.

10. The system of claim 1, wherein the operations further comprise:

determining a first contour of an ROI in the registered planning image volume and a second contour of the ROI in the registered treatment image volume;

determining a first intersection plane between a reference plane and the first contour and a second intersection plane between the reference plane and the second contour;

generating a comparison result between the ROI in the registered planning image volume and the ROI in the registered treatment image volume based on the first intersection plane and the second intersection plane; and evaluating, based on the comparison result, whether an error exists in at least one of the registration or the contour determination.

11. The system of claim 10, wherein the comparison result relates to a similarity between the first intersection plane and the second intersection plane.

12. A method for adaptive treatment planning implemented on a computing device having at least one processor and at least one storage device, the method comprising:

obtaining a planning image volume of a subject, a treatment image volume of the subject, and a first treatment plan related to the planning image volume of the subject;

obtaining a determination result by determining, based on the planning image volume and the treatment image volume, whether the first treatment plan needs to be modified, in response to the determination result that the first treatment plan needs to be modified, generating a modified treatment plan by modifying the first treatment plan;

obtaining an evaluation result by evaluating whether an error exists in the generation of the modified treatment plan by:
  registering the planning image volume and the treatment image volume with respect to a common coordinate system;
  identifying one or more planes in an overlapping volume between the registered planning image volume and the registered treatment image volume, the one or more planes passing through one or more characteristic spots in the registered planning image volume; and
  obtaining the evaluation result based on one or more characteristic spots on the one or more planes in the registered treatment image volume; and
generating, based on the evaluation result, a second treatment plan with respect to the treatment image volume.

13. The method of claim 12, wherein the generating, based on the evaluation result, a second treatment plan with respect to the treatment image volume comprises:
  in response to the evaluation result that error exists in the generation of the modified treatment plan, generating the second treatment plan by further modifying the modified treatment plan or modifying the first treatment plan; or
  in response to the evaluation result that no error exists in the generation of the modified treatment plan, designating the modified treatment plan as the second treatment plan.

14. The method of claim 12, wherein the obtaining a determination result by determining, based on the planning image volume and the treatment image volume, whether the first treatment plan needs to be modified comprises:
  determining a first contour of an ROI in the registered planning image volume and a second contour of the ROI in the registered treatment image volume; and
  determining, based on the first contour and the second contour, whether the first treatment plan needs to be modified.

15. The method of claim 14, wherein the method further comprises:
  generating a comparison result between the ROI in the planning image volume and the ROI in the treatment image volume by comparing the first contour and the second contour; and
  evaluating, based on the comparison result, whether a second error exists in at least one of the registration or the contour determination.

16. The method of claim 15, wherein the comparison result relates to at least one of:
  a volume difference between a volume of the ROI in the registered treatment image volume and a volume of the ROI in the registered planning image volume, or
  a surface area difference between a volume of the ROI in the registered treatment image volume and a volume of the ROI in the registered planning image volume.

17. The method of claim 15, wherein the generating the comparison result comprises:
  determining a first intersection plane between a reference plane and the first contour;
  determining a second intersection plane between the reference plane and the second contour; and
  determining a similarity between the first intersection plane and the second intersection plane.

18. A method for adaptive treatment planning implemented on a computing device having at least one processor and at least one storage device, the method comprising:
  obtaining a planning image volume of a subject, a treatment image volume of the subject, and a first treatment plan related to the planning image volume of the subject;
  obtaining a determination result by determining, based on the planning image volume and the treatment image volume, whether the first treatment plan needs to be modified,
  in response to the determination result that the first treatment plan needs to be modified, generating a modified treatment plan by modifying the first treatment plan;
  obtaining an evaluation result by evaluating whether an error exists in the generation of the modified treatment plan by:
    determining a registration matrix by registering the planning image volume and the treatment image volume with respect to a common coordinate system;
    determining one or more characteristic spots in the registered planning image volume;
    determining, based on the registration matrix and the one or more characteristic spots in the registered planning image volume, one or more characteristic spots in the registered treatment image volume; and
    obtaining the evaluation result based on the one or more characteristic spots in the registered treatment image volume; and
  generating, based on the evaluation result, a second treatment plan with respect to the treatment image volume.

19. The method of claim 18, wherein the obtaining a determination result by determining, based on the planning image volume and the treatment image volume, whether the first treatment plan needs to be modified comprises:
  determining a first contour of an ROI in the registered planning image volume and a second contour of the ROI in the registered treatment image volume; and
  determining, based on the first contour and the second contour, whether the first treatment plan needs to be modified.

20. The method of claim 19, wherein the determining the second contour of the ROI in the registered treatment image volume comprises:
  determining, based on the registration matrix and the first contour of the ROI in the registered planning image volume, the second contour of the ROI in the registered treatment image volume.

* * * * *